(12) United States Patent
Bliss et al.

(10) Patent No.: US 9,295,794 B2
(45) Date of Patent: Mar. 29, 2016

(54) VARIABLE FLOW OXYGEN THERAPY

(75) Inventors: Peter Bliss, Prior Lake, MN (US);
Robert Murdoch, Kennesaw, GA (US);
Robert Romano, Pittsburgh, PA (US);
Peter D. Hill, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1007 days.

(21) Appl. No.: 13/131,622

(22) PCT Filed: Nov. 21, 2009

(86) PCT No.: PCT/IB2009/055252
§ 371 (c)(1),
(2), (4) Date: May 27, 2011

(87) PCT Pub. No.: WO2010/070493
PCT Pub. Date: Jun. 24, 2010

(65) Prior Publication Data
US 2011/0232642 A1    Sep. 29, 2011

Related U.S. Application Data

(60) Provisional application No. 61/122,908, filed on Dec. 16, 2008.

(51) Int. Cl.
*F16K 31/02* (2006.01)
*A61M 16/00* (2006.01)
*A61M 16/06* (2006.01)
*A61M 16/10* (2006.01)

(52) U.S. Cl.
CPC ........... *A61M 16/00* (2013.01); *A61M 16/0677* (2014.02); *A61M 16/101* (2014.02); *A61M 2016/0015* (2013.01); *A61M 2016/1025* (2013.01); *A61M 2202/0208* (2013.01)

(58) Field of Classification Search
CPC   A61M 16/00; A61M 16/0677; A61M 16/101
USPC ........................................ 128/204.18, 204.21
See application file for complete search history.

(56) References Cited

U.S. PATENT DOCUMENTS

| 4,686,974 | A |   | 8/1987 | Sato | |
|---|---|---|---|---|---|
| 5,660,171 | A | * | 8/1997 | Kimm et al. | 128/204.23 |
| 5,735,267 | A | * | 4/1998 | Tobia | 128/204.21 |
| 5,735,268 | A |   | 4/1998 | Chua | |
| 5,813,399 | A | * | 9/1998 | Isaza et al. | 128/204.21 |
| 6,568,391 | B1 | * | 5/2003 | Tatarek et al. | 128/204.26 |
| 2001/0035185 | A1 | * | 11/2001 | Christopher | 128/204.17 |
| 2002/0040714 | A1 |   | 4/2002 | Yagi | |
| 2006/0201505 | A1 | * | 9/2006 | Remmers et al. | 128/204.21 |
| 2008/0178880 | A1 | * | 7/2008 | Christopher et al. | 128/204.23 |

FOREIGN PATENT DOCUMENTS

| WO | WO9640336 A2 | 12/1996 |
|---|---|---|
| WO | WO9922795 A1 | 5/1999 |

* cited by examiner

*Primary Examiner* — Justine Yu
*Assistant Examiner* — Kathrynn Lyddane
(74) *Attorney, Agent, or Firm* — Michael W. Haas (57) ABSTRACT

The present invention describes systems and methods to provide variable flow oxygen therapy. An exemplary embodiment of the present invention provides a method of oxygen therapy involving delivering oxygen-enriched gas to a patient during a first portion of a breathing cycle at a first flow rate. Furthermore, the method of oxygen therapy involves delivering oxygen-enriched gas to the patient during a second portion of the breathing cycle at a second flow rate, where the second flow rate is greater than zero and less than the first flow rate.

7 Claims, 8 Drawing Sheets

VARIABLE FLOW OXYGEN THERAPY

CROSS-REFERENCE TO RELATED APPLICATIONS

This patent application claims the priority benefit under 35 U.S.C. §119(e) of U.S. Provisional Application No. 61/122,908 filed on Dec. 16, 2008, the contents of which are herein incorporated by reference.

BACKGROUND OF THE INVENTION

1. Field of the Invention

The present invention relates generally to systems and methods for providing oxygen therapy and, more particularly, to systems and methods for providing variable flow oxygen therapy.

2. Description of the Related Art

A growing number of people in the United States suffer from chronic obstructive pulmonary disease (COPD) such as asthma and emphysema, as well as cystic fibrosis, lung cancer, lung injuries, cardiovascular diseases, and otherwise diseased or damaged lungs. Although there is no cure for many of these conditions, their detrimental impact of can be mitigated by the prescription of oxygen therapy. The inhalation of oxygen-enriched gas serves to compensate for the poor function of the patient's lungs in absorbing oxygen.

More and more people are using oxygen therapy outside the hospital, permitting them to lead active, productive lives. Recent developments in oxygen therapy technology have given those dependent upon oxygen a variety of in-home and portable options for oxygen therapy. There are three main ways to personally administer oxygen therapy outside of a medical facility, (1) oxygen concentrators, (2) liquid oxygen devices, and (3) compressed gas devices. Each of these three types of solutions provide particular benefits and detriments.

First, oxygen concentrators or pressure swing adsorption systems are an excellent source of oxygen therapy for in home use. Pressure swing adsorption ("PSA") systems are advantageous in that they can process ambient air, containing approximately 21% oxygen, and separate that oxygen from the ambient air. Thereby the user can be supplied with higher concentrations of oxygen. While suitable for their intended purpose, oxygen concentrators are generally bulky and require access to a power source, such as an electrical outlet. Thus, oxygen concentrators are ill-suited for portability and are not intended for use with an ambulatory individual.

Second, liquid oxygen system ("LOX" system) can provide a convenient method of portable oxygen therapy. Liquid oxygen is advantageous because it occupies significantly less space of compressed gaseous oxygen. A conventional LOX system includes a large stationary LOX storage canister that stays in the home. The conventional system also includes a small, portable delivery apparatus that can be filled from the stationary unit for trips outside the home. Many first generation systems have limited utilization due to the low LOX capacity of the portable delivery apparatus and the administered LOX flow rate. To maintain a liquid state, oxygen must be kept at a relatively cool temperature around 300 degrees Fahrenheit below zero. Therefore, the liquid oxygen stored in LOX systems will evaporate even if not used by the user. In this manner, the LOX system has a relatively short use period that expires regardless of whether the user is actually using the oxygen.

Third, compressed oxygen systems are generally prescribed when oxygen is not needed all the time, such as only when walking or performing physical activity. Small compressed oxygen tanks are well suited for portability in that they can be relatively light weight and they can maintain their supply of oxygen when not in use. Small portable compressed oxygen devices are limited, however, in how long they will last depending on the prescribed flow rate and type of tank. Therefore, portable compressed oxygen devices must be refilled often.

While suitable for their intended purposes, conventional oxygen delivery devices suffer from many drawbacks. For example, many conventional oxygen delivery devices are unable to provide oxygen delivery at different flow rates. Furthermore, existing oxygen delivery devices cannot provide phasic oxygen delivery at various flow rates. Moreover, conventional pulse mode devices can irritate the patient, especially when the patient is attempting to go to sleep. Additionally, many conventional devices are unable to provide a reliable and sustained method of backup oxygen delivery.

SUMMARY OF THE INVENTION

Accordingly, it is an object of the present invention to provide an oxygen therapy that overcomes the shortcomings of conventional oxygen therapies. This object is achieved according to one embodiment of the present invention by providing systems and methods to provide variable flow oxygen therapy. An exemplary embodiment of the present invention provides a method of oxygen therapy involving delivering oxygen-enriched gas to a patient during a first portion of a breathing cycle at a first flow rate. Furthermore, the method of oxygen therapy involves delivering oxygen-enriched gas to the patient during a second portion of the breathing cycle at a second flow rate, where the second flow rate is greater than zero and less than the first flow rate.

In addition, the present invention provides methods for backup oxygen therapy. An exemplary embodiment of a method of oxygen therapy involves detecting a loss of synchronization based on the lack of a breathing cycle trigger for a predetermined alarm period. Furthermore, the method of oxygen therapy requires activating a backup mode of oxygen therapy, which involves delivering oxygen-enriched gas to the patient for a predetermined backup pulse period and sensing for a breathing cycle trigger for a predetermined sensing period.

These and other objects, features and advantages of the present invention will become more apparent upon reading the following specification in conjunction with the accompanying drawing figures.

DETAILED DESCRIPTION OF THE EXEMPLARY EMBODIMENTS

The present invention addresses the deficiencies in the existing concerning the inability of conventional oxygen delivery devices to provide for variable phasic delivery of oxygen. Significantly, the present invention provides methods and apparatus for oxygen therapy involving the phasic delivery of variable flow rates of oxygen. Additionally, the present invention overcomes the drawbacks of the conventional methods and systems and provides systems and methods enabled to provide efficient backup modes for oxygen delivery devices when synchronization is lost with the patient's breathing cycle.

An exemplary embodiment of the present invention provides a method of oxygen therapy involving delivering oxygen-enriched gas to a patient during a first portion of a breathing cycle at a first flow rate. Furthermore, the method of oxygen therapy involves delivering oxygen-enriched gas to the patient during a second portion of the breathing cycle at a second flow rate, where the second flow rate is greater than zero and less than the first flow rate.

In addition, the present invention provides methods for backup oxygen therapy. An exemplary embodiment of a method of oxygen therapy involves detecting a loss of synchronization based on the lack of a breathing cycle trigger for a predetermined alarm period. Furthermore, the method of oxygen therapy requires activating a backup mode of oxygen therapy, which involves delivering oxygen-enriched gas to the patient for a predetermined backup pulse period and sensing for a breathing cycle trigger for a predetermined sensing period.

One of the significant advantages provided by oxygen therapy system in accordance with the present invention is the ability to provide a variable flow rate of oxygen to the patient that is synchronized with the breathing cycle of patient. Furthermore, the method of oxygen therapy provided by the present invention enables for continuous oxygen delivery to the patient at a variable flow rate and the ability to independently modify the flow rate two or more times during a breathing cycle of the patient.

Figure 7:
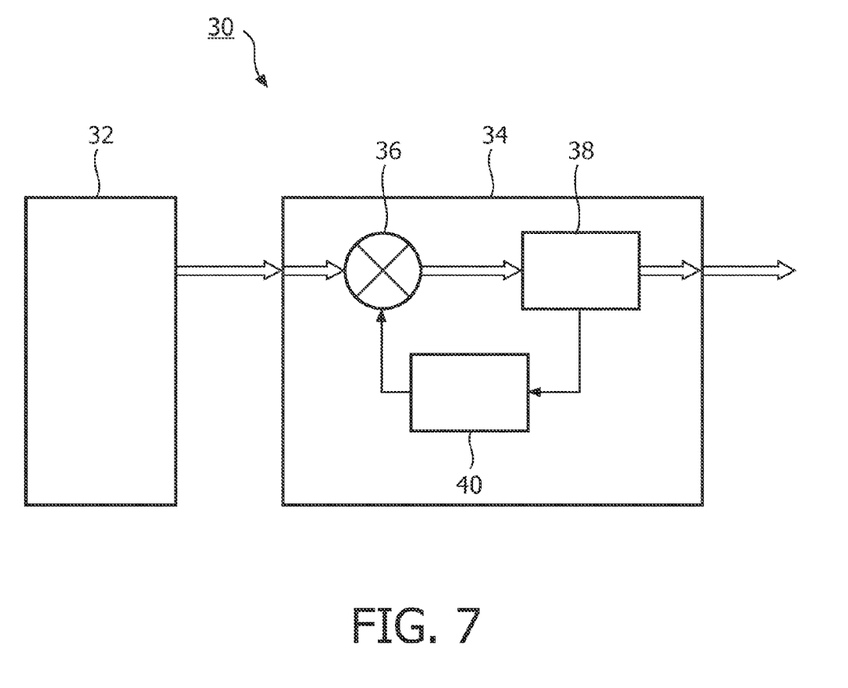
FIG. 7 is an exemplary embodiment of an oxygen delivery system suitable for use in providing the oxygen therapies according to the principles of the present invention.

The present invention contemplates that the oxygen therapies or modes of providing oxygen to a patient are implemented by any suitable oxygen delivery system that is capable of controlling the follow of oxygen delivered to the patient in a feed back fashion. An example of such a system is described in U.S. Pat. No. 7,370,651, the contents of which are incorporated herein by reference. FIG. 7 also schematically illustrates another example of such an oxygen delivery system 30.

As shown in FIG. 7, oxygen delivery system 30 includes a source of oxygen 32, such as an oxygen concentrator, a pressurized supply of gaseous oxygen contained in a pressurized vessel, or a supply of liquid oxygen. Oxygen delivery system 30 includes a flow control system 34 that control the flow, volume, and/or pressure of gas delivered from gas source 32 to a patient. Flow control system 34 includes a flow control assembly 36, such as a valve, that controls the flow, volume, or pressure of gas provided by source of oxygen 32 to a user. A controller 40 controls flow control assembly 36 to deliver the oxygen to a user as discussed herein. That is, controller 40 implements the method of oxygen therapy according to the principles of the present invention. One or more sensors 38 are provided to monitor the user, the oxygen delivery system or both, and provide signals to controller 40.

Flow control system 34 can be implemented as a stand-alone system that attaches oxygen source 32, such as by being physically mounted onto the stem of an oxygen tank in fluid communication with the gas stored in the tank. Alternatively, flow control system 34 can be provided in the same housing as oxygen source 32. If, for example, oxygen source 32 is an oxygen concentrator or a portable liquid oxygen delivery system, flow control system 34 can be provided in the same housing containing the components of the oxygen concentrator or the portable liquid oxygen delivery system. This implement is similar to the manner in which conventional oxygen conservers are provided in existing oxygen delivery systems.

Figure 1:
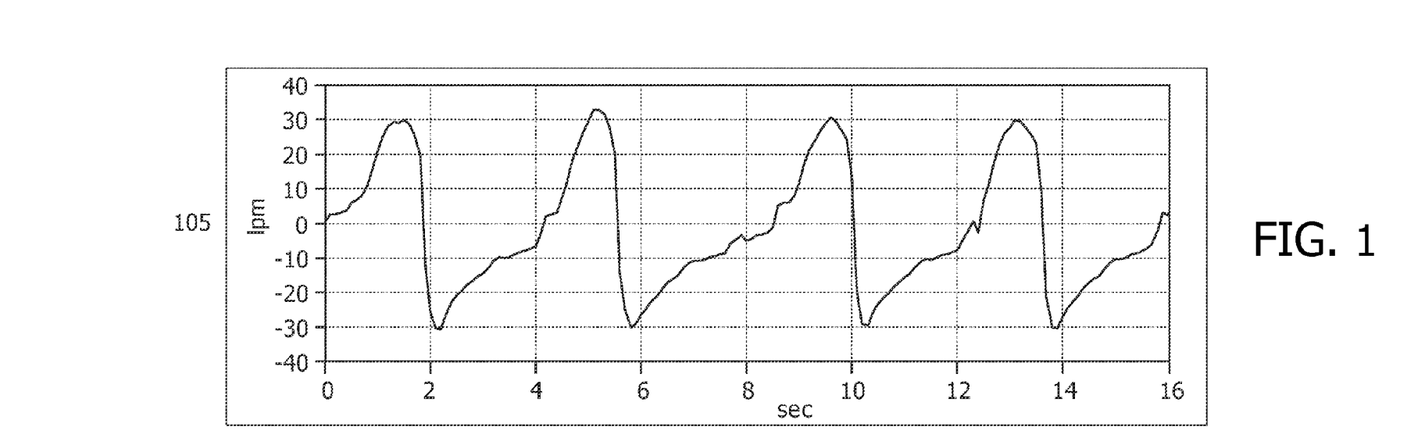
FIG. 1 and FIG. 1A are patient flow diagrams of the variable flow method of oxygen therapy provided in accordance with an exemplary embodiment of the present invention as compared to conventional oxygen delivery methods.
Figure 1A:
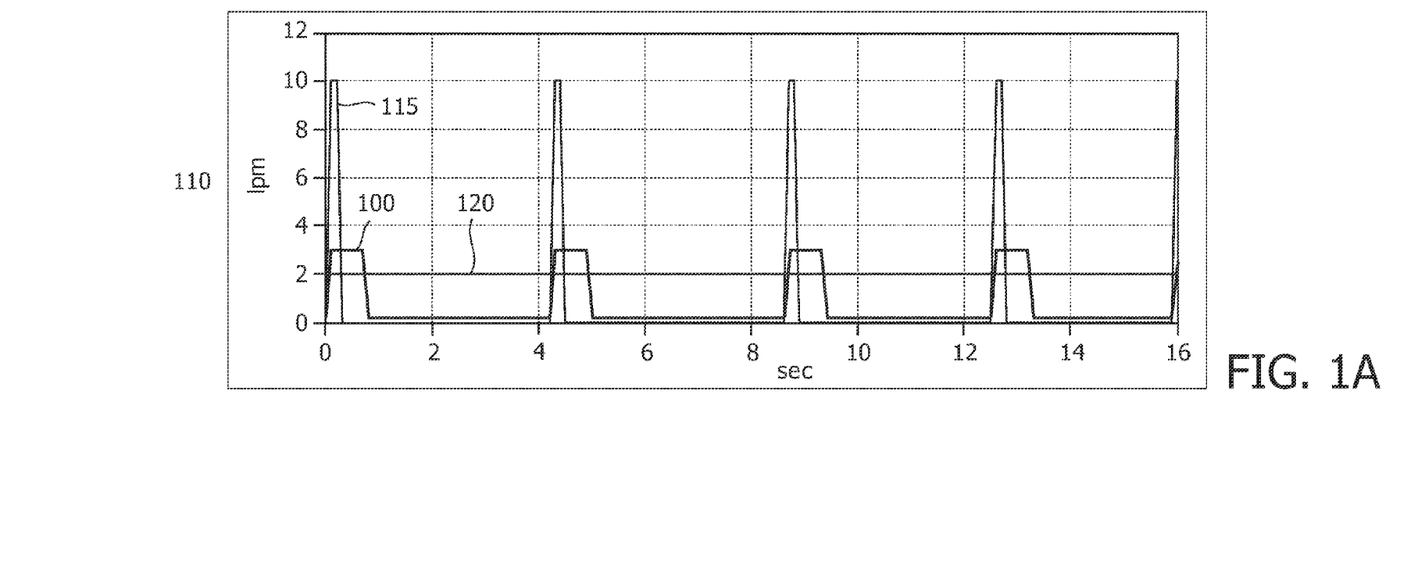

Referring now to FIG. 1A, this figure illustrates a patient flow diagram of the variable flow method of oxygen therapy 100 provided in accordance with an exemplary embodiment of the present invention as compared to conventional oxygen delivery methods. As shown in FIG. 1, the flow diagram 105 illustrates an exemplary embodiment of the breathing flow of a breathing cycle of a patient. In flow diagram 105, a positive flow rate (liters per minute, "LPM") represents inspiration by the patient and a negative flow rate represents expiration by the patient. The combination of one inspiratory phase and one expiratory phase represent one breathing cycle by the patient. The flow diagram 110 shown in FIG. 1A illustrates various methods of oxygen therapy including the variable flow method of oxygen therapy 100.

As shown in FIG. 1A, with a conventional pulse method of oxygen therapy 115, oxygen is delivered in a large and relatively instantaneous bolus to the patient. Typically, in the conventional pulse method of oxygen therapy 115, the pulse is triggered around the beginning of the inspiratory phase of the breathing cycle of the patient. Therefore, the patient receiving the conventional pulse method of oxygen therapy 115 receives oxygen at a relatively high flow rate, such as 10 LPM shown in FIG. 1A, for a relatively short period of time, such as just a portion of the initial part of the inspiratory phase of the breathing cycle of the patient as shown in FIG. 1A.

As shown in FIG. 1A, with the conventional continuous flow of oxygen method of oxygen therapy 120, oxygen is delivered at a constant flow rate throughout the breathing cycle of the patient. In the example show in FIG. 1A, the conventional continuous flow of oxygen method of oxygen therapy 120 delivers oxygen at a constant flow rate of 2 LPM. Therefore, regardless of the phase of the breathing cycle, the conventional continuous flow of oxygen method of oxygen therapy 120 delivers a constant stream of oxygen to the patient.

The variable flow method of oxygen therapy 100 shown in FIG. 1A illustrates the manner in which oxygen is delivered to the patient in accordance with an exemplary embodiment of the present invention. In an exemplary embodiment of the variable flow method of oxygen therapy 100, a variable flow of oxygen is provided to the patient in synchronization with the breathing cycle 105 shown in FIG. 1. As shown in diagram 110 of the FIG. 1A, the variable flow method of oxygen therapy 100 can be configured to deliver a higher flow rate of oxygen to the patient during a first portion of a patient's breathing cycle and lower flow rate of oxygen to the patient during a second portion of the patient's breathing cycle. In an exemplary embodiment shown in FIG. 1A, the first portion of the breathing cycle can be a portion of an inspiratory phase of the breathing cycle and the second portion of the breathing cycle can be a portion of the expiratory phase of the breathing cycle.

In an exemplary embodiment, the present invention provides an oxygen delivery device enabled to implement both the variable flow method of oxygen therapy 100 and a conventional pulse method of oxygen therapy 115. Therefore, in an exemplary embodiment an oxygen delivery device has both a first mode of oxygen delivery and second mode of oxygen delivery. The first mode of oxygen delivery can correspond to the conventional pulse method of oxygen therapy 115 in an exemplary embodiment, wherein a first volume of oxygen-enriched gas is delivered during a portion of inhalation at a first flow rate for a first predetermined period of time. The second mode of oxygen delivery can correspond to the variable flow method of oxygen therapy 100, wherein a second volume of oxygen-enriched gas is delivered during a portion of inhalation at a second flow rate for a second predetermined period of time during.

In an exemplary embodiment, the first volume and second volume can be equivalent, but the second predetermined period of time can be longer than the first predetermined period of time. Thus, the amount of oxygen-enriched gas delivered during a portion of the inspiratory cycle can be equivalent, but in the second mode a lower flow rate of oxygen-enriched gas is delivered over a longer period of time. In an exemplary embodiment of the oxygen delivery system, the first mode of oxygen delivery corresponds to active mode, useful for when the patient is active, and the second mode of oxygen delivery corresponds to a resting or sleep mode, for when the patient is inactive.

FIG. 1A illustrates the various modes of an oxygen delivery device in an exemplary embodiment, in which first mode of oxygen delivery corresponds to the conventional pulse method of oxygen therapy 115 and the second mode of oxygen delivery corresponds to the variable flow method of oxygen therapy 100. Thereby, the delivery of oxygen illustrated by the conventional pulse method of oxygen therapy 115 illustrates oxygen delivery for an active patient by the oxygen delivery device in an exemplary embodiment. Similarly, the delivery of oxygen illustrated by the variable flow method of oxygen therapy 100 illustrates oxygen delivery for a resting patient by the oxygen delivery device in an exemplary embodiment.

One of the advantages provided by the present invention is that it enables a more comfortable yet still efficient phasic oxygen delivery method than those provided by conventional devices. As shown in FIG. 1A, the conventional pulse method of oxygen therapy 115 delivers a relatively large bolus of oxygen to the patient in a fast dose. The rush of injected oxygen that occurs with the conventional pulse method of oxygen therapy 115 can be irritating to a patient, especially when the patient is trying to go to sleep. For example, a patient receiving the conventional pulse method of oxygen therapy 115 can have difficulty going to sleep with a rush of oxygen being delivered into the patient's breathing passageway every couple of seconds. Both the sound and the sensation can be irritating to the patient. The variable flow method of oxygen therapy 100 enabled by the present invention can facilitate the onset of sleep by providing non-irritating phasic oxygen delivery. For example, and not limitation, the variable flow method of oxygen therapy 100 can deliver a first flow rate of oxygen during an inspiratory phase of the breathing cycle, and the first flow rate can be sufficiently low so as not to present an annoyance to the patient. Therefore, the dosage flow rate of an exemplary embodiment of the variable flow method of oxygen therapy 100 can be a comfortable flow rate for the patient.

As shown in FIG. 1A, the conventional pulse method of oxygen therapy 115 can deliver a bolus of oxygen at around 10 LPM, while the variable flow method of oxygen therapy 100 can provide oxygen at a flow rate of around 3 LPM. Thereby, a patient receiving an exemplary embodiment of the variable flow method of oxygen therapy 100 is much less likely to notice or be irritated by the 3 LPM delivery of oxygen gas as compared to the conventional pulse method of oxygen therapy 115 delivery of gas at almost three times that flow rate. Those of skill in the art will appreciate that various flow rates of an exemplary embodiment of the variable flow method of oxygen therapy 100 can be configured according to the different parameters of the patient and the equipment being used. Some patient's may require more oxygen and some patients may not be as irritated by a higher flow rate of oxygen.

Therefore, in accordance with an exemplary embodiment of the present invention, an oxygen delivery device can be provided with a "comfort mode," that enables the device to deliver oxygen in accordance with variable flow method of oxygen therapy 100. In an exemplary embodiment of this oxygen delivery device, the patient can have option to utilize the "comfort mode" when sleeping or resting and utilize a conventional pulse method of oxygen therapy 115 when engaging in activities.

The variable flow method of oxygen therapy 100 can be configured in an exemplary embodiment to synchronize with the breathing cycle such that oxygen is delivered at a higher flow rate at the beginning of an inspiratory phase. Thereafter, oxygen delivery can be reduced to a lower flow rate for the remainder of the inspiratory phase and the expiratory phase of the breathing cycle in an exemplary embodiment of the variable flow method of oxygen therapy 100. As shown in diagram 110 of FIG. 1A, the flow rate during the last portion of the inspiratory phase and the expiratory phase can be close to zero, such as 0.1 to 0.5 LPM.

Figure 1B:
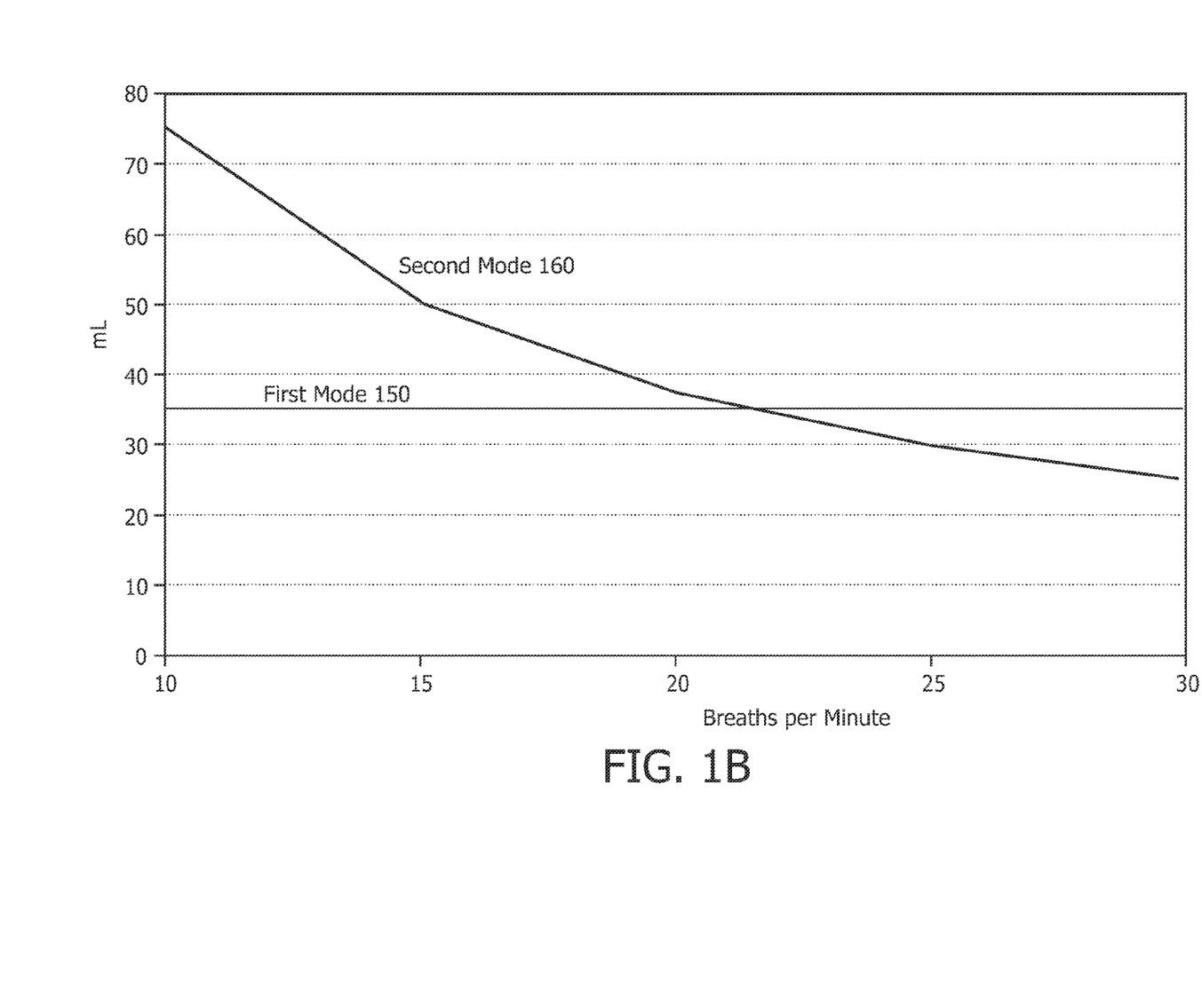
FIG. 1B provides a diagram of the volume of oxygen delivered by the oxygen delivery device provided in accordance with an exemplary embodiment of the present invention.

FIG. 1B provides a diagram of the volume of oxygen delivered by the oxygen delivery device provided in accordance with an exemplary embodiment of the present invention. An exemplary embodiment of the oxygen delivery device enabled by the present invention can deliver oxygen in two different modes. FIG. 1B illustrates the volume of oxygen-enriched gas (shown on the y-axis) delivered by an exemplary embodiment of the oxygen delivery device in both a first mode of oxygen delivery 150 and a second mode of oxygen delivery 160 versus the breathing rate of the patient, breaths per minute (shown on the x-axis). As shown in FIG. 1B, in an exemplary embodiment the first mode of oxygen delivery 150 can provide a constant volume of oxygen to the patient regardless of the breathing rate of the patient. For example, and not limitation, the first mode of oxygen delivery 150 shown in FIG. 1B, can provide a constant volume of 35 mL of oxygen-enriched gas to the patient regardless of breathing rate.

As shown in exemplary embodiment in FIG. 1B, the second mode of oxygen delivery 160 can provide a variable volume of oxygen to the patient in accordance with the breathing rate of the patient. More particularly, in an exemplary embodiment, the second mode of oxygen delivery 160 can be configured to be inversely proportional to the breathing rate of the patient. Therefore, in this exemplary embodiment, when the breathing rate of the patient slows down, such as when the patient is sleeping, the volume of oxygen-enriched gas delivered to the patient by the oxygen delivery device operating in the second mode of oxygen delivery 160 can be increased. For example, and not limitation, the second mode of oxygen delivery 160 shown in FIG. 1B, can provide 30 mL of oxygen-enriched gas to the patient when the patient is breathing at 25 breaths per minute and can provide 50 mL of oxygen-enriched gas when the patient is breathing at 15 breaths per minute. Thus, a patient is enabled to receive more oxygen per breath when resting with an exemplary embodiment of the oxygen delivery device.

Figure 2:
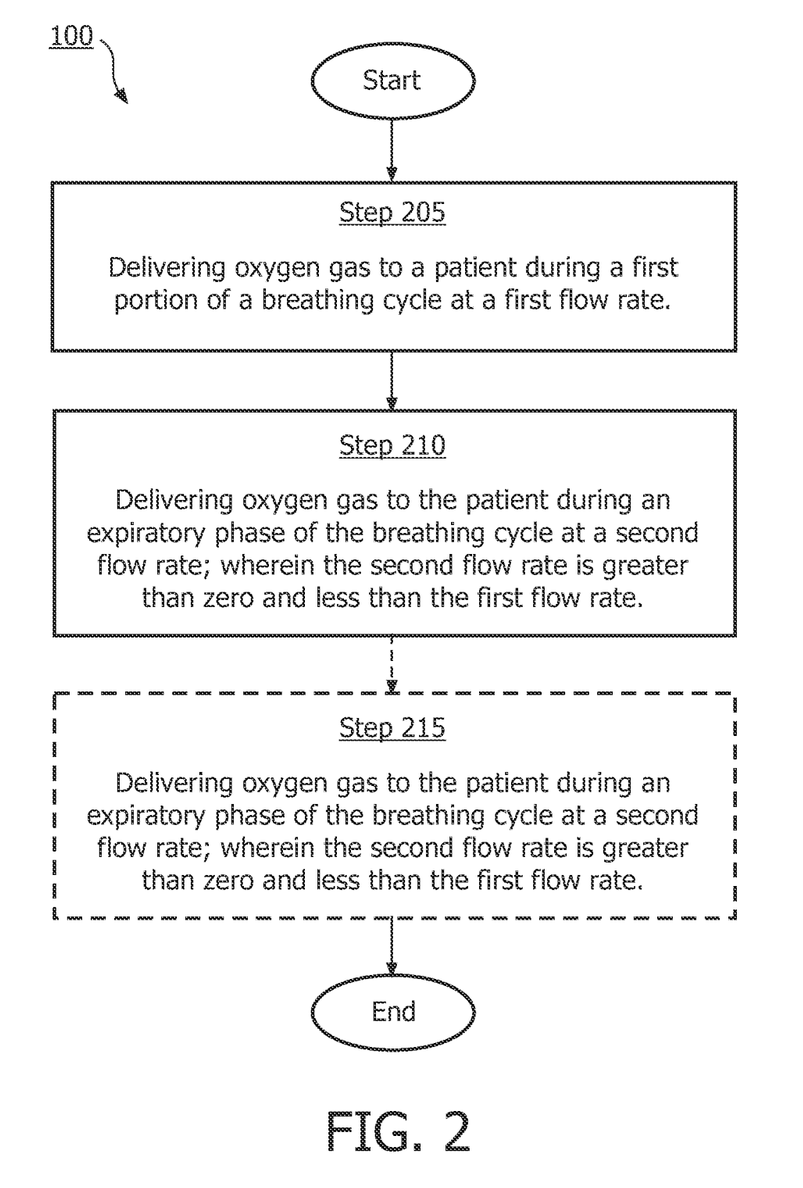
FIG. 2 provides a block diagram for the variable flow method of oxygen therapy provided in accordance with an exemplary embodiment of the present invention.

FIG. 2 provides a block diagram for the variable flow method of oxygen therapy 100 provided in accordance with an exemplary embodiment of the present invention. In an exemplary embodiment of the variable flow method of oxygen therapy 100, a first step 205 involves delivering oxygen gas to a patient during a first portion of a breathing cycle at a first flow rate. In an exemplary embodiment, s second step 210 of the variable flow method of oxygen therapy 100 involves delivering oxygen gas to the patient during a second portion of the breathing cycle at a second flow rate, where the second flow rate is greater than zero and less than the first flow rate. Therefore, in an exemplary embodiment oxygen gas can be delivered at a higher flow rate during a portion of the inspiratory phase than the remainder of the breathing cycle. Thus, in an exemplary embodiment a relatively high rate of oxygen can be delivered to the patient during the initial portion of inspiration and then a lower rate of oxygen can be delivered to the patient during the end of the inspiration phase and during the expiratory phase of the breathing cycle.

One of the significant benefits provided by an exemplary embodiment of the variable flow method of oxygen therapy 100 is that it enables oxygen to be variably supplied to the patient. For example, and not limitation, oxygen can be supplied to the patient during the expiration phase of the breathing cycle to permit the patient to benefit from the pooling of oxygen in the patient's breathing passageway. It is appreciated that typically when a patient exhales, a certain amount of the exhaled gas containing $CO_2$ remains in the anatomical deadspace of the patient's breathing passageway. Thus, the next time the patient begins to inhale, the exhaled gas is rebreathed by the patient. An exemplary embodiment of the variable flow method of oxygen therapy 100 enables oxygen to be delivered to the patient during exhalation such that a certain amount of oxygen pools in the anatomical deadspace of the patient's breathing passageway. Therefore, the initial gas received into the patient's lungs under an exemplary embodiment of the variable flow method of oxygen therapy 100 can contain a higher percentage of oxygen.

Those of skill in the art will appreciate that the ability to provide a variable flow of oxygen to the patient can provide numerous benefits. In certain implementations, it may be advantageous to alter the flow rate of oxygen provided to the patient three or more times during the breathing cycle. In an alternative embodiment of the variable flow method of oxygen therapy 100, shown in dashed lines in FIG. 2, a third step 215 is added to the variable flow method of oxygen therapy 100. In the alternative embodiment, s third step 215 involves the delivery of oxygen gas at a third flow rate during a third portion of the breathing cycle. The third flow rate, in the alternative embodiment, can be greater than the second flow rate and less than the first flow rate. The ability to provide a third flow rate during a third portion of the breathing cycle can provide a number of different benefits. For example, and not limitation, the third flow could be selected such that a slightly higher amount of oxygen is provided to the patient at the end of an expiratory phase such that oxygen is pooled in the anatomical deadspace of the patient's breathing passageway just before the patient begins a new inspiratory phase.

In the exemplary embodiment of the variable flow method of oxygen therapy 100 shown in FIG. 1A, a first step 205 of delivering oxygen gas to a patient during a first portion of a breathing cycle at a first flow rate can be set to be triggered by an event in the breathing cycle. For example, and not limitation, first step 205 can be triggered by the onset on the inspiratory cycle. Thus, when the beginning of inspiration is detected in this exemplary embodiment, oxygen can be delivered at a first flow rate. In an exemplary embodiment, the method of oxygen therapy 100 can be implemented by an oxygen delivery device with cannula. In this embodiment, the trigger can be configured based on a drop in pressure in the cannula. For example, and not limitation, the trigger can be set to initiate first step 205 of the method of oxygen therapy 100 when the cannula pressure drops below a threshold value. In some embodiments, triggering is made more difficult by the possibility of confusing one of the flow rates of oxygen-enriched gas delivered to the patient for a triggering change in pressure, such a backpressure in the cannula. Those of skill in the art will appreciate that false triggers can be avoided by proper configuration of the baselines for various triggers and/or the addition of certain components, such as a flow sensor.

In one example, the first flow rate is referred to as the Inspiration flow or Iflow. Iflow can vary upon implementation, but in the exemplary embodiment shown in FIG. 1A, Iflow is set to be the 3 LPM. In this example, the higher flow rate can serve to augment the continuous flow oxygen pooled during the later portion an expiratory phase of the breathing cycle. In an exemplary embodiment, Iflow can be described as follows:

$$Iflow = DoseSetting \times 1.5 \text{ LPM}$$

Thus, Iflow can depend upon the recommend dose setting for a particular patient. In this example implementation, the second step 210 of the variable flow method of oxygen therapy 100 can deliver oxygen gas to the patient during a second portion of the breathing cycle at a second flow rate. In the exemplary embodiment of the variable flow method of oxygen therapy 100 shown in FIG. 1A, this second portion of the breathing cycle occurs after an initial portion of the inspiratory phase of the breathing cycle.

Those of skill in the art will appreciate that in other implementations of the variable flow method of oxygen therapy 100 the second portion could occur during the transition to the expiratory phase, during the expiratory phase, or at other portions of the breathing cycle. In one example, the second flow rate is referred to as the Expiratory flow or Eflow. Eflow can be set according to the parameters for a given implementation. For example, and not limitation, Eflow can be set at a continuous flow rate, such as 0.2 LPM. In an other example, Eflow can be variable and linearly increase up to the end of an expiratory phase of the breathing cycle. Eflow can be accounted for in oxygen delivery systems, which sense an increase in pressure as a trigger to the beginning of an inspiratory phase of a breathing cycle.

Figure 3:
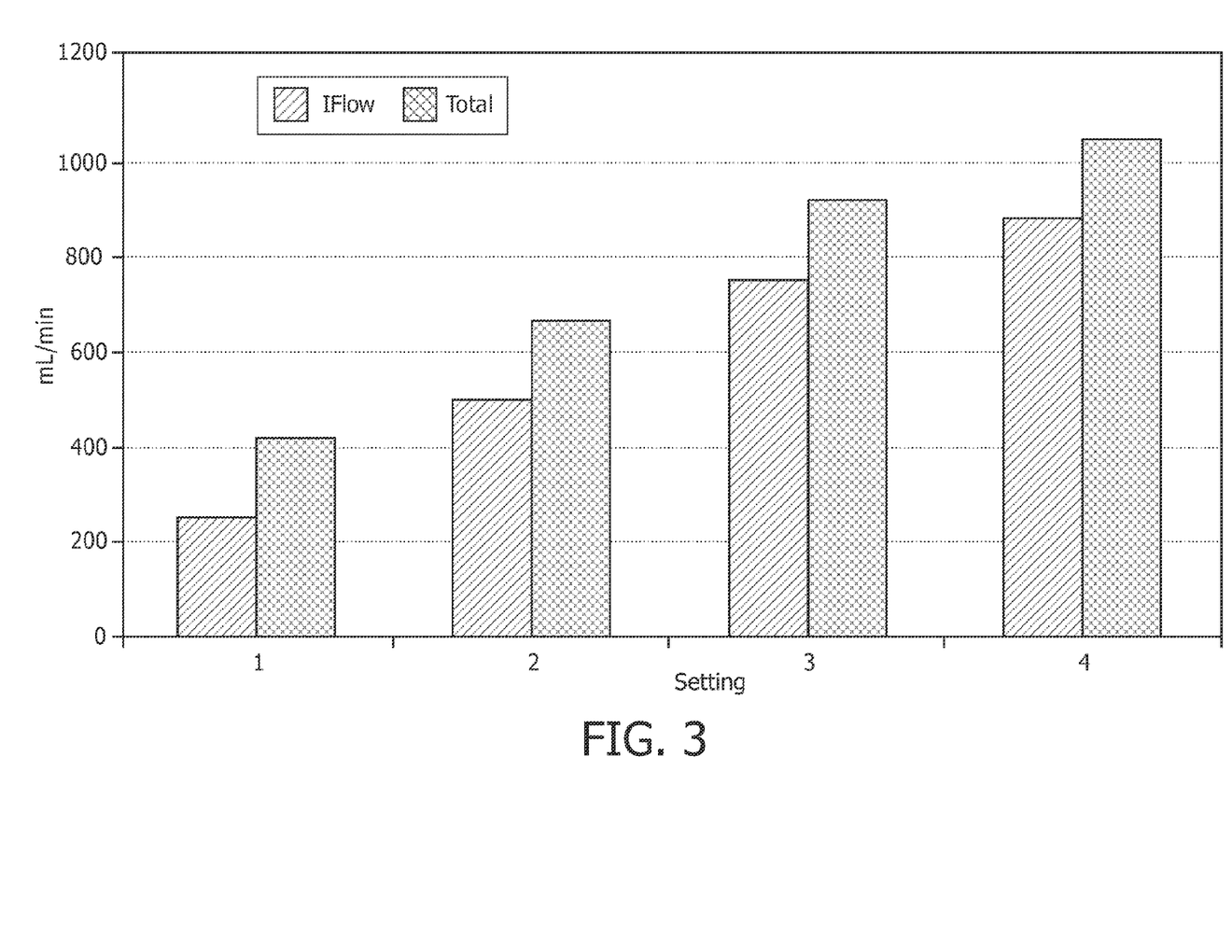
FIG. 3 provides a diagram of the oxygen delivered by an oxygen delivery system configured in accordance with an exemplary embodiment of the present invention.

FIG. 3 provides a diagram of the oxygen delivered by an oxygen delivery system configured in accordance with an exemplary embodiment of the present invention. In an exemplary embodiment, the period of time for Iflow can be decreased as breath rate increases. Therefore, in this embodiment the total minute volume of oxygen required from the oxygen source of the oxygen delivery system can remain constant across all breathing rates.

As shown in FIG. 3, the dose setting of the oxygen delivery system can determine volume of oxygen-enriched gas that is delivered to the patient. For example, and not limitation, when the oxygen delivery system is set to a dose setting of 1, the Iflow portion of the oxygen delivery can provide around 0.225 LPM. The Eflow rate can be set according to the parameters of a desired implementation. In the example depicted in FIG. 3, when the oxygen delivery system can be configured to deliver at a constant rate of 0.2 LPM. Thus, the total amount of oxygen delivered to the patient on a dose setting of one is around 0.425 LPM, shown in the second bar graph for dose setting of one in FIG. 3. As shown in FIG. 3, when the oxygen delivery system is set to a dose setting of 2, the Iflow portion of the oxygen delivery can provide around 0.5 LPM. Furthermore, as shown in FIG. 3, at a dose setting of 2, the amount of oxygen-enriched gas delivered during Iflow essentially doubles to 0.5 LPM. The oxygen delivery system can continue to provide oxygen-enriched gas at a constant rate of 0.2 LPM during Eflow; thus, the total oxygen delivery rate is around 0.7 LPM.

In an exemplary embodiment of the oxygen delivery system, the system can have a delivery capacity of 1.05 LPM. Therefore, in this exemplary embodiment the maximum dose setting for the oxygen delivery system should be 3.5 when the Eflow is set to be constant at a rate of 0.2 LPM, which corresponds to a total delivery rate of around 0.9 LPM. When the Eflow is set to be constant at a rate of 0, the maximum dose setting for the oxygen delivery system can be 4, as this corresponds to a total delivery rate of around 0.875 LPM. Those of skill in the are will appreciate, that the maximum dose setting can increased in oxygen delivery systems with a higher maximum delivery capacity such as a 2 LPM delivery capacity.

Figure 4:
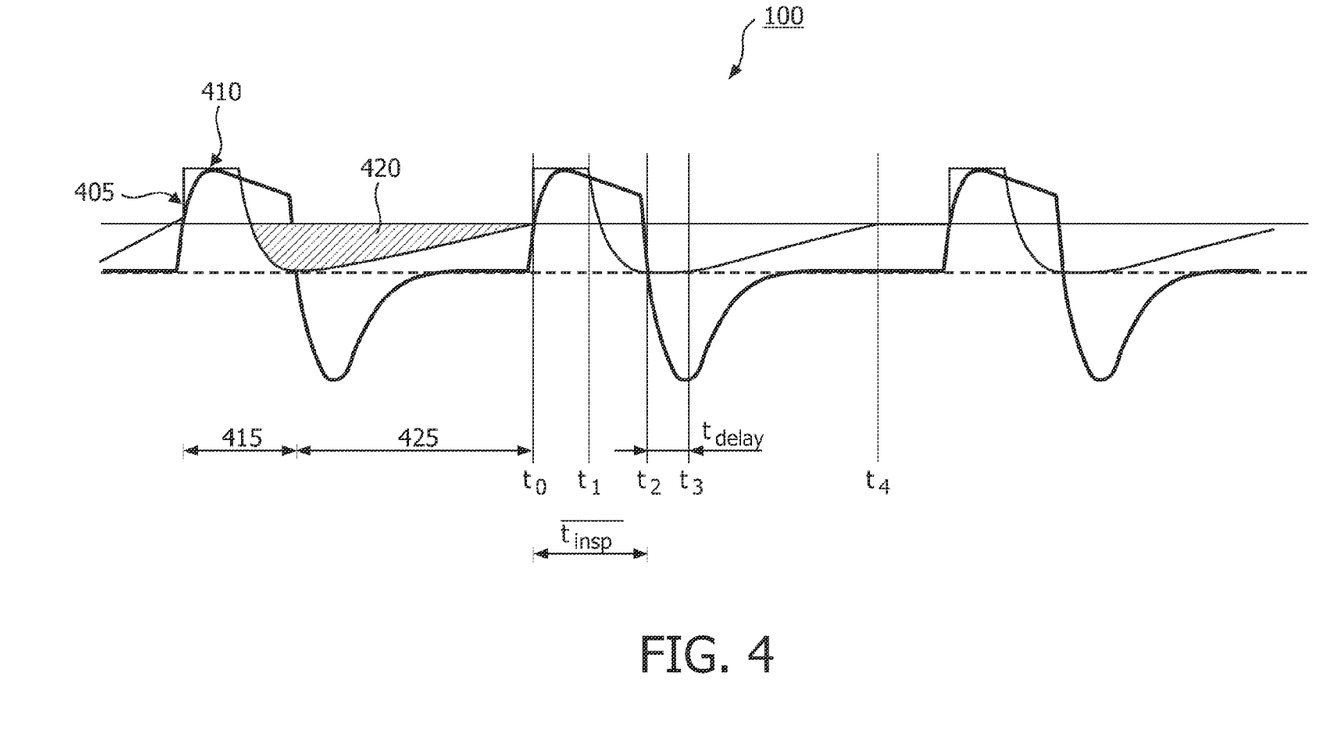
FIG. 4 provides a patient flow diagram of the variable flow method of oxygen therapy provided in accordance with an exemplary embodiment of the present invention.

FIG. 4 provides a patient flow diagram of the variable flow method of oxygen therapy 100 provided in accordance with an exemplary embodiment of the present invention. As shown in FIG. 4, the variable flow method of oxygen therapy 100 can enable for oxygen to be delivered to the patient at a rate that varies in accordance with the patient's breathing cycle 405. A first flow rate of oxygen 410 can be delivered to the patient during a first portion 415 of the breathing cycle 405. As shown in the exemplary embodiment in FIG. 4, the first portion 415 of the breathing cycle 405 can correspond to the inspiratory phase. Therefore, as shown in the exemplary embodiment in FIG. 4, the variable flow method of oxygen therapy 100 can be triggered by the inspiratory phase of the breathing cycle 405.

Additionally, a second flow rate 420 of oxygen can be delivered to the patient during a second portion 425 of the breathing cycle 405. Second portion 425 of the breathing cycle 405 in an exemplary embodiment can correspond, as shown in FIG. 4, to the expiratory phase of the breathing cycle 405. Second flow rate 420 of an exemplary embodiment of the variable flow method of oxygen therapy 100 can be a variable flow rate as shown in FIG. 4. Therefore, second flow rate 420 can linearly increase during the expiratory phase of breathing cycle 405. The ability to provide variable flow rates of oxygen delivery can provide numerous advantages for the patient. For example, and not limitation, the gradually increasing second flow rate 420 of the exemplary embodiment of the variable flow method of oxygen therapy 100 shown in FIG. 4 can aid in dissipating exhaled $CO_2$ and enable oxygen-enriched gas to pool in the anatomical deadspace of the patient's breathing passageway.

In an exemplary embodiment of the present invention a method of oxygen therapy is provided that enables a backup mode of oxygen therapy. A backup mode of oxygen therapy is often required for phasic oxygen delivery methods when synchronization is lost with the breathing cycle of the patient. An exemplary embodiment of the present invention enables a backup mode of oxygen delivery that can still enable resynchronization with the breathing cycle of the patient.

Figure 5:
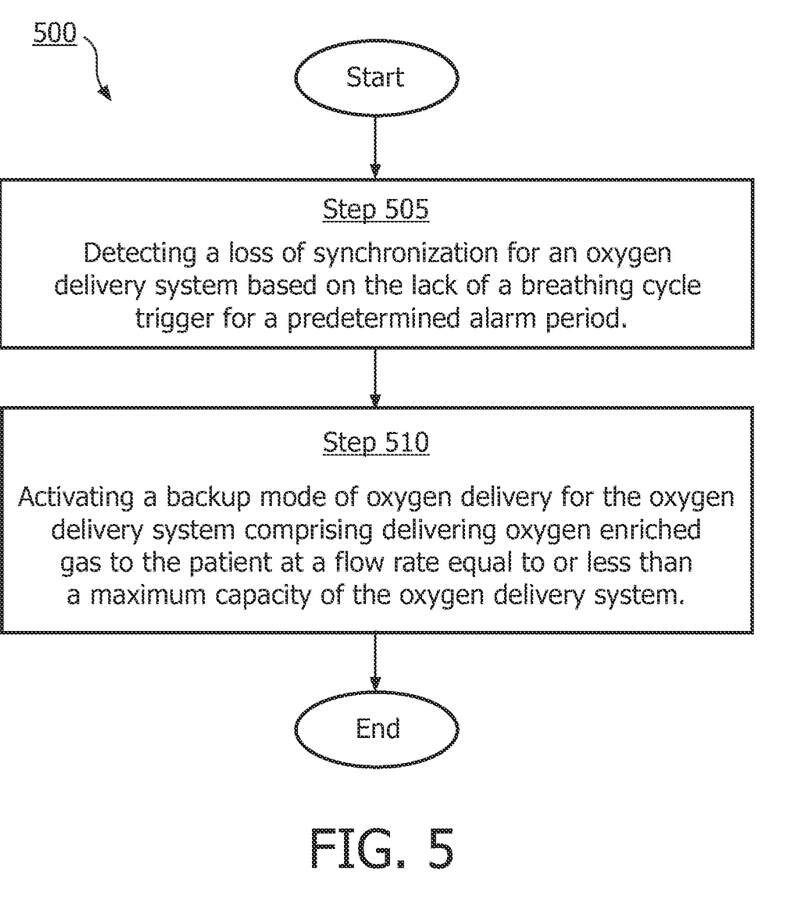
FIG. 5 provides a block diagram for the method of backup oxygen delivery provided in accordance with an exemplary embodiment of the present invention.

FIG. 5 provides a block diagram for the method of backup oxygen delivery 500 provided in accordance with an exemplary embodiment of the present invention. In an exemplary embodiment of the method of backup oxygen delivery 500, a first step 505 involves detecting a loss of synchronization based on the lack of a breathing cycle trigger for a predetermined alarm period. The term loss of synchronization is used herein to indicate when a system is no longer able to detect a trigger of a synchronizing component of a patient's breathing cycle. Those of skill in the art will appreciate that the breathing cycle trigger can be a variety of different trigger parameters, such as the onset of the inspiratory phase or the onset of the expiratory phase of the breathing cycle. When there is a loss of synchronization, oxygen therapy can no longer be provided in sequence with the breathing cycle of the patient. The second step 510 of the method of backup oxygen delivery 500 involves activating a backup mode of oxygen delivery for the oxygen delivery system comprising delivering oxygen-enriched gas to the patient at a flow rate equal to or less than a maximum capacity of the portable oxygen delivery system.

One of the significant advantages of the method of backup oxygen delivery 500 is that it permits a portable oxygen delivery system to provide reliable backup oxygen delivery without exceeding the capacity of the oxygen delivery system. Thus, when synchronization with a patient's breathing cycle is lost, an oxygen delivery device operating in accordance with an exemplary embodiment of the method of backup oxygen delivery 500 can enter a backup mode of oxygen delivery in which a constant flow of oxygen-enriched gas is delivered to the patient at a flow rate equal to or less than a maximum capacity of the oxygen delivery system. This is especially important in the area of portable oxygen delivery device, including portable oxygen concentrators. For example, and not limitation, many portable oxygen concentrators can be set to delivery oxygen at the equivalent of 3 LPM, but the portable oxygen concentrators is not enabled to deliver a continuous supply of oxygen enriched gas at 3 LPM, but rather achieves the equivalent of 3 LPM with a pulse delivery to the patient. Thus, the maximum sustained capacity for the portable oxygen concentrator may be 2 LPM or even 1 LPM. In an exemplary embodiment of the method of backup oxygen delivery 500, the backup mode can be configured so as not exceed the maximum sustained of the portable oxygen concentrator.

For example, and not limitation, a portable oxygen concentrator with a maximum sustained delivery rate of 1 LPM can be configured to deliver a constant flow of 1 LPM of oxygen-enriched gas to the patient during the backup mode of oxygen delivery. Those of skill in the art will appreciate that different oxygen delivery systems have different oxygen delivery capacities; thus, the flow rate during backup mode can vary from device to device. Some conventional devices provide a backup mode of oxygen delivery, but they do not limit the delivery of oxygen in accordance with maximum sustained delivery capacity of the oxygen delivery device. These conventional devices, are therefore unable to provide a consistent and reliable method of backup oxygen delivery.

Even though the method of backup oxygen delivery 500 may provide oxygen below the recommended or prescribed therapeutic oxygen flow rate for a patient, it can still provide effective oxygen therapy. An exemplary embodiment of the method of backup oxygen delivery 500 can still be therapeutic because oxygen therapy is exponentially less effective as the flow rate of oxygen increases. For example, and not limitation, in an exemplary embodiment the backup mode of oxygen delivery provides oxygen at 1 LPM, the maximum sustained oxygen delivery rate of the oxygen delivery system of the exemplary embodiment. In this exemplary embodiment, the patient's prescribed oxygen flow rate may be 3 LPM, but in backup mode the patient only receives 1 LPM. The delivery of oxygen in the backup mode in this exemplary embodiment, however, is therapeutic as the patient may be receiving a majority of the oxygen therapy required even though that patient is only receiving ⅓ of the prescribed flow rate.

Figure 6:
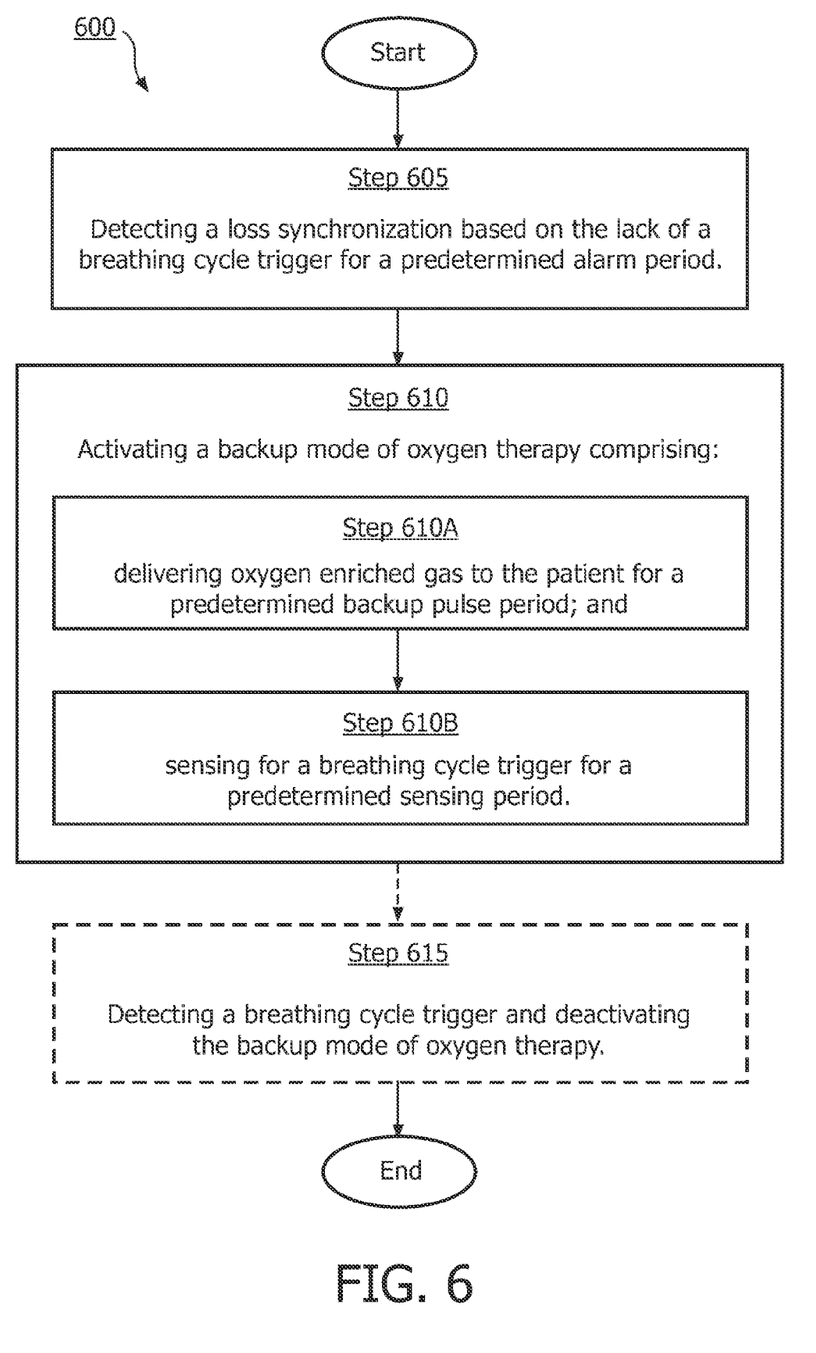
FIG. 6 provides a block diagram for the method of backup oxygen delivery provided in accordance with an exemplary embodiment of the present invention.

FIG. 6 provides a block diagram for the method of backup oxygen delivery 600 provided in accordance with an exemplary embodiment of the present invention. In an exemplary embodiment of the method of backup oxygen delivery 600, a first step 605 involves determining a loss of synchronization based on the lack of a breathing cycle trigger for a predetermined alarm period. When there is a loss of synchronization, oxygen therapy can no longer be provided in sequence with the breathing cycle of the patient.

In an exemplary embodiment, the breathing cycle trigger can be a variety of different trigger parameters such as the onset of the inspiratory phase or the onset of the expiratory phase of the breathing cycle. A second step 610 of the method of backup oxygen delivery 600 involves activating a backup mode of oxygen therapy. An exemplary embodiment of the method of backup oxygen delivery 600 enables a backup mode of oxygen delivery to be activated after the patient's breath is not sensed for a certain period of time, a predetermined alarm period. In an exemplary embodiment, the predetermined alarm period is equal to three average breathing cycles. In an exemplary embodiment of the method of backup oxygen delivery 600, the backup mode can deliver either a continuous flow or an asynchronous flow of timed pulses of oxygen delivery and then sense for the patient's breath cycle during a sensing period.

In the exemplary embodiment depicted in FIG. 6, the backup mode of oxygen therapy involves a first sub-step 610A of delivering oxygen-enriched gas to the patient for a predetermined backup pulse period. Additionally, the backup mode of oxygen therapy involves a second sub-step 610B of sensing for a breathing cycle trigger for a predetermined sensing period. In an exemplary embodiment, if a breathing cycle trigger is not sensed during the predetermined sensing period, the method can require the return to the first sub-step 610A of delivering oxygen-enriched gas to the patient for a predetermined backup pulse period. Thus, the method of backup oxygen delivery 600 can iteratively delivery oxygen to the patient in a backup mode and simultaneously attempt to resynchronize with the patient's breathing cycle.

In an alternative embodiment of the method of backup oxygen delivery 600, shown in dashed lines in FIG. 6, a third step 615 is added to the method of backup oxygen delivery 600. This third step 615 involves detecting a breathing cycle trigger and deactivating the backup mode of oxygen therapy. Therefore, the alternative embodiment of the method of backup oxygen delivery 600 can provide a method of exiting the backup mode of oxygen delivery in the event that synchronization with the patient's breathing cycle can be regained. In an alternative embodiment of the method of backup oxygen delivery 600, the backup mode of oxygen delivery can be reestablished if synchronization is subsequently lost with the patient. Thus, the various embodiments of the method of backup oxygen delivery 600 can enable reliable and efficient backup mode oxygen delivery, and, at the same time, enable resynchronization with the patient's breathing cycle.

The method of backup oxygen delivery 600 can be configured for a variety of backup mode operations. In an exemplary embodiment, the backup mode is a timed operation in which oxygen is delivered during Iflow for a predetermined pulse period and sensing is conducted for a predetermined sensing period during Eflow. In this exemplary embodiment, oxygen can be continuously delivered at various flow rates to the patient in a backup mode, and the system can still attempt to resynchronize with the patient's breathing cycle. In another exemplary embodiment, the backup mode is a continuous oxygen delivery mode with a pause period for sensing. Therefore, in an exemplary embodiment of the continuous mode method of backup oxygen delivery 600, oxygen is delivered for a predetermined pulse period and then stopped while sensing is conducted during a predetermined sensing period.

It can be appreciated that the present invention provides an apparatus and method for the phasic oxygen delivery with a reliable backup mode of oxygen delivery. In addition, the present invention provides a safe and efficient method of backup oxygen delivery.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing oxygen therapy using an oxygen delivery system, the method comprising:
    delivering oxygen-enriched gas to a patient during a first portion of a breathing cycle at a first flow rate, wherein delivering oxygen-enriched gas during the first portion is triggered by an inspiratory phase of the breathing cycle, and wherein:
        the oxygen-enriched gas is enriched with oxygen so the oxygen level of the oxygen-enriched gas is greater than the oxygen level of ambient air;
        the first flow rate is constant for a pre-determined period of time within the first portion; and
        the first flow rate is reduced to zero during the remainder of the first portion; and
    delivering oxygen-enriched gas to the patient during a second portion of the breathing cycle at a second flow rate, the second portion corresponding to an expiratory phase of the breathing cycle, wherein the second flow rate is greater than zero and less than the constant first flow rate delivered during the pre-determined period of time and wherein the second flow rate is a variable flow rate that increases linearly during the second portion of the breathing cycle, and wherein the first portion and the second portion are consecutive portions and correspond to the breathing cycle of the patient.

2. An oxygen delivery system comprising:
    a housing; and
    an oxygen source in communication with the housing, wherein the oxygen source is enabled to deliver oxygen-enriched gas to a patient during a first portion of a breathing cycle at a first flow rate, wherein delivering oxygen-enriched gas during the first portion is triggered by an inspiratory phase of the breathing cycle wherein:

the oxygen-enriched gas is enriched with oxygen so the oxygen level of the oxygen-enriched gas is greater than the oxygen level of ambient air, and the first flow rate is constant for a pre-determined period of time within the first portion; and the first flow rate is reduced to zero during the remainder of the first portion; and wherein the oxygen source is enabled to deliver oxygen-enriched gas to the patient during a second portion of the breathing cycle at a second flow rate, the second portion corresponding to an expiratory phase of the breathing cycle, wherein the second flow rate is greater than zero and less than the constant first flow rate delivered during the pre-determined period of time, and wherein the second flow rate is a variable flow rate that increases linearly during the second portion of the breathing cycle, and wherein the first portion and the second portion are consecutive portions and correspond to the breathing cycle of the patient.

3. The oxygen delivery system of claim 2, further comprising a flow sensor enabled to control the flow rate of oxygen delivered to the patient.

4. The oxygen delivery system of claim 2, wherein the oxygen source is further enabled to deliver oxygen-enriched gas to the patient during a third portion of the breathing cycle at a third flow rate, wherein the third flow rate is greater than the second flow rate and less than the first flow rate, and wherein the first portion, the second portion, and the third portion are consecutive portions and correspond to the breathing cycle of the patient.

5. An oxygen delivery system comprising:

a housing;

an oxygen source in communication with the housing, wherein the oxygen source is enabled to deliver oxygen-enriched gas to a patient wherein the oxygen-enriched gas is enriched with oxygen so the oxygen level of the oxygen-enriched gas is greater than the oxygen level of ambient air;

the oxygen source being enabled to be switched between a first mode of oxygen delivery and a second mode of oxygen delivery;

the first mode of oxygen delivery comprises delivering a first volume of oxygen-enriched gas at a constant first flow rate for a first predetermined period of time, and then reducing the first flow rate to zero, wherein delivering the first volume of oxygen-enriched gas is triggered by an inspiratory phase of the breathing cycle;

the second mode of oxygen delivery comprises delivering a second volume of oxygen-enriched gas at a second flow rate for a second predetermined period of time, the second predetermined period of time corresponding to an expiratory phase of the breathing cycle; and wherein the second flow rate is greater than zero and less than the first flow rate and the second predetermined period of time is greater than the first predetermined period of time and wherein the second flow rate is a variable flow rate that increases linearly during the second predetermined period of time.

6. The method of claim 1 wherein the oxygen level of the oxygen-enriched gas is more than 21% oxygen.

7. The system of claim 2 wherein the oxygen level of the oxygen-enriched gas is more than 21% oxygen.

\* \* \* \* \*